(12) United States Patent
Hossainy et al.

(10) Patent No.: US 6,585,765 B1
(45) Date of Patent: Jul. 1, 2003

(54) IMPLANTABLE DEVICE HAVING SUBSTANCES IMPREGNATED THEREIN AND A METHOD OF IMPREGNATING THE SAME

(75) Inventors: Syed F. A. Hossainy, Fremont, CA (US); Jacqueline Ghio, San Carlos, CA (US); Li Chen, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 69 days.

(21) Appl. No.: 09/608,444

(22) Filed: Jun. 29, 2000

(51) Int. Cl.⁷ .............................. A61F 2/06; A61L 29/00
(52) U.S. Cl. ...................... 623/1.45; 623/66; 427/2.24
(58) Field of Search .................................. 623/1.43, 1.46, 623/1.18, 1.42, 1.44, 66, 907; 124/422, 423, 424; 427/2.22, 2.24, 2.25, 2.3

(56) References Cited

U.S. PATENT DOCUMENTS

| | | | |
|---|---|---|---|
| 4,459,252 A | 7/1984 | MacGregor | 264/46.9 |
| 5,059,211 A | 10/1991 | Stack et al. | 606/198 |
| 5,163,952 A | 11/1992 | Froix | 623/1 |
| 5,306,286 A | 4/1994 | Stack et al. | 606/198 |
| 5,527,337 A | 6/1996 | Stack et al. | 606/198 |
| 5,700,286 A | 12/1997 | Tartaglia et al. | 623/1 |
| 5,713,949 A | 2/1998 | Jayaraman | 623/1 |
| 5,766,710 A | 6/1998 | Turnlund et al. | 428/36.1 |
| 5,769,883 A | 6/1998 | Buscemi et al. | 623/1 |
| 5,843,172 A | 12/1998 | Yan | 623/1 |
| 5,873,904 A | 2/1999 | Ragheb et al. | 623/1 |
| 6,120,536 A | 9/2000 | Ding et al. | 623/1.43 |
| 6,120,847 A | 9/2000 | Yang et al. | 427/335 |
| 6,206,915 B1 | 3/2001 | Fagan et al. | 623/1.42 |
| 6,287,628 B1 | 9/2001 | Hossainy et al. | 427/2.3 |
| 6,379,381 B1 | 4/2002 | Hossainy et al. | 623/1.42 |

FOREIGN PATENT DOCUMENTS

| | | | |
|---|---|---|---|
| EP | 0 850 651 | 7/1998 | |
| EP | 0 875 218 | 11/1998 | |
| JP | 11299901 | 11/1999 | |
| WO | WO 90/01969 | 3/1990 | |
| WO | WO 98/23228 | 6/1998 | ............. A61F/2/06 |
| WO | WO 99/16386 | 4/1999 | |

*Primary Examiner*—David J. Isabella
(74) *Attorney, Agent, or Firm*—Squire, Sanders & Dempsey, L.L.P.

(57) ABSTRACT

The present invention provides a method of impregnating an implantable device, such as a vascular graft or a covering adapted to be disposed over a prosthesis. The substances may be impregnated within the implantable device as a passive coating or as a delivery matrix for a therapeutic substance. Also provided is an implantable device having such substances impregnated therein.

52 Claims, 5 Drawing Sheets

IMPLANTABLE DEVICE HAVING SUBSTANCES IMPREGNATED THEREIN AND A METHOD OF IMPREGNATING THE SAME

BACKGROUND OF THE INVENTION

1. Field of the Invention

The present invention relates generally to implantable devices, such as synthetic vascular grafts and covered stents. More particularly, the present invention is directed to a method of impregnating an implantable device with substances as well as to an implantable device that has been so impregnated.

2. Description of the Related Art

Occlusion of blood vessels reduces or blocks blood flow. During the course of atherosclerosis, for example, growths called plaques develop on the inner walls of the arteries and narrow the bore of the vessels. An embolis, or a moving clot, is more likely to become trapped in a vessel that has been narrowed by plaques. Further, plaques are common sites of thrombus formation. Together, these events increase the risk of heart attacks and strokes.

Traditionally, critically stenosed atherosclerotic vessels have been treated with bypass surgery in which veins removed from the legs, or small arteries removed from the thoracic cavity, are implanted in the affected area to provide alternate routes of blood circulation. More recently, implantable devices, such as synthetic vascular grafts and stents, have been used to treat diseased blood vessels.

Synthetic vascular grafts are macro-porous vessel-like configurations typically made of expanded polytetrafluoroethylene (ePTFE), polyethylene terephthalate (PET), polyurethane (PU), or an absorbable polymer. Grafts made of ePTFE or PET are very non-wetting materials when introduced into an aqueous environment, causing difficulty in impregnating the materials. In addition, grafts made of ePTFE or PET are permanently implanted in the body, while grafts made of an absorbable polymer bioabsorb over time. A graft may be positioned into the host blood vessel as a replacement for a diseased or occluded segment that has been removed. Alternatively, a graft may be sutured to the host vessel at each end so as to form a bypass conduit around a diseased or occluded segment of the host vessel.

Intravascular stents may be permanently or temporarily implanted in narrowing blood vessels. Typically, a vascular catheter, or similar transluminal device, is utilized to carry the stent to the treatment site. The stent is expanded to support, and if desired expand, the diseased portion of the arterial wall. The insertion of a stent into a vessel in which plaque has become brittle over time, however, may cause complications if the stent causes the brittle plaque to break off from the vessel wall and embolize the lumen. A covered stent, in which a graft-like covering is slip-fit onto the stent, may therefore be employed to isolate the brittle plaque from direct contact with the stent, which is rigid.

To treat such damaged vasculature tissue and to help prevent thrombosis and restenosis, there is a need for administering therapeutic substances to the treatment site. To provide an efficacious concentration to the treatment site, systemic administration of the therapeutic substance often produces adverse or toxic side effects for the patient. Local delivery is a highly suitable method of treatment, in that smaller levels of therapeutic substances, as compared to systemic dosages, are concentrated at a specific site. Local delivery produces fewer side effects and achieves more effective results.

One technique for the local delivery of therapeutic substances is through the use of medicated coatings on implantable devices. In addition to providing local delivery capabilities, such a coating protects vessel tissue from injury and helps prevent excessive foreign body reaction that may occur when such a device is implanted.

SUMMARY OF THE INVENTION

The present invention provides a method by which implantable devices, including those made of very non-wetting materials, may be impregnated with passive as well as therapeutic substances. An implantable device that has been impregnated with such substances is also provided.

In accordance with one embodiment of the present invention, a method of impregnating an implantable device, such as a vascular graft or a covering adapted to be disposed over a prosthesis, is provided. The method includes an act of providing a substrate having a body and interstices throughout the body, an act of applying a composition containing a first substance and a first fluid to the substrate such that the composition penetrates into the interstices of the body of the substrate, and an act of removing essentially all of the first fluid from the composition within the body of the substrate. The first substance remains within the body of the substrate. An implantable device having a first substance deposited therein in accordance with the above-described method is also provided.

In some embodiments of the method described herein, the first substance is a pre-polymer. In such embodiments, the method further includes the act of causing the pre-polymer to crosslink to form a hydrogel within the body of the substrate. In addition, an implantable device having a hydrogel formed therein in accordance with the method is provided.

In other embodiments of the above-described method, the body of the substrate has a first end, an opposing second end, and a hollow bore extending longitudinally through the body from the first end to the second end. In such embodiments, the method may further include the act of providing a prosthesis and the act of inserting the prosthesis at least partially within the hollow bore of the body of the substrate. In some embodiments, the prosthesis has a plurality of depots formed therein. In such embodiments, the act of providing a prosthesis may further include the act of forming the plurality of depots within the prosthesis. The act of providing a prosthesis may also include the act of depositing a second substance within the plurality of depots. The deposited material may be selected from therapeutic substances, polymeric materials, and radiopaque materials, among other possibilities.

In other embodiments of the above-described method, prior to applying the composition, the method additionally includes an act of applying a second fluid to the substrate. In other embodiments, subsequent to applying the second fluid and prior to applying the composition, the method additionally includes an act of applying a third fluid to the substrate. In still other embodiments, the method additionally includes an act of applying a bridging fluid to the substrate between the otherwise consecutive application of immiscible fluids.

In other embodiments of the above-described method, the composition additionally includes a therapeutic substance. The therapeutic substance is selected from a group of antineoplastic, antimitotic, antiplatelet, anticoagulant, fibrinolytic, thrombin inhibitor, antiinflammatory and antiproliferative, antioxidant, and antiallergic substances, and mixtures thereof.

Also disclosed is an implantable device. The device includes a substrate having a body and interstices within the body. The body has a first end, an opposing second end, and a hollow bore extending longitudinally through the body from the first end to the second end. The device also includes a first substance impregnated within the interstices of the body of the substrate and a prosthesis inserted at least partially within the hollow bore of the body of the substrate. The prosthesis has a plurality of depots formed therein. In some embodiments of the implantable device, the plurality of depots contain a second substance.

These and other aspects of the present invention may be better appreciated in view of the detailed description and drawings of the exemplary embodiments.

DETAILED DESCRIPTION OF THE EMBODIMENTS

The following definitions apply hereinthroughout unless a contrary intention is expressly indicated:

"Crosslink" means to attach a polymer chain to another polymer chain or to a monomer by lateral bonds with or without the assistance of crosslinking agents and/or energy in the form of electromagnetic radiation and/or heat;

"Miscible" means that two liquids are capable of being mixed in at least some proportions, and is inclusive of fully miscible systems that are capable of being mixed in all proportions without phase separation, as well as partially miscible systems that are capable of being mixed in some, but not all, proportions;

"Polymer," "poly," and "polymeric" mean the product of a polymerization reaction and are inclusive of homopolymers, copolymers, terpolymers etc., whether natural or synthetic, including random, alternating, block, graft, crosslinked, blends, compositions of blends and variations thereof; and "Pre-polymer" means a reactive polymer that has not yet been crosslinked.

Figure 1A:
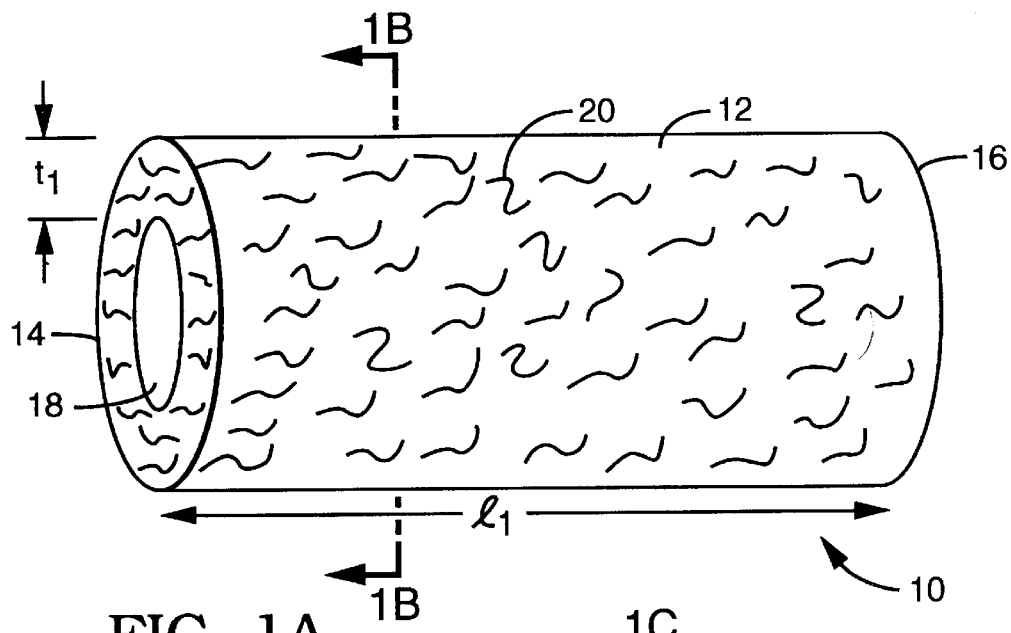
FIG. 1A illustrates a perspective view of an implantable device with a central hollow bore.
Figure 1B:
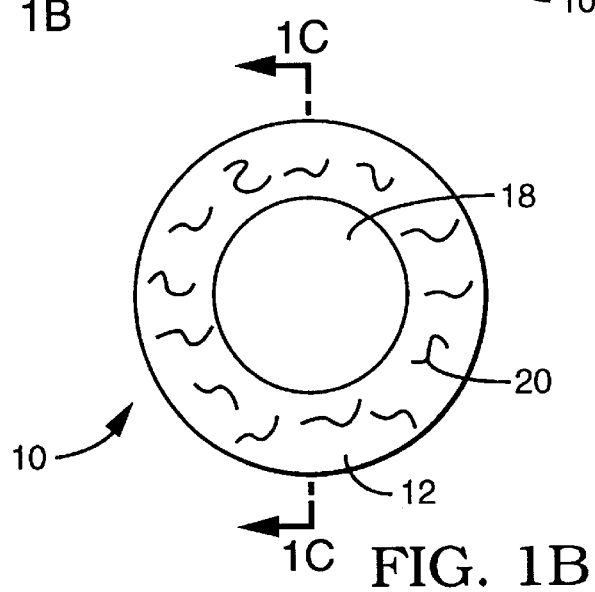
FIG. 1B illustrates a cross-section taken along line 1B—1B of FIG. 1A.
Figure 1C:
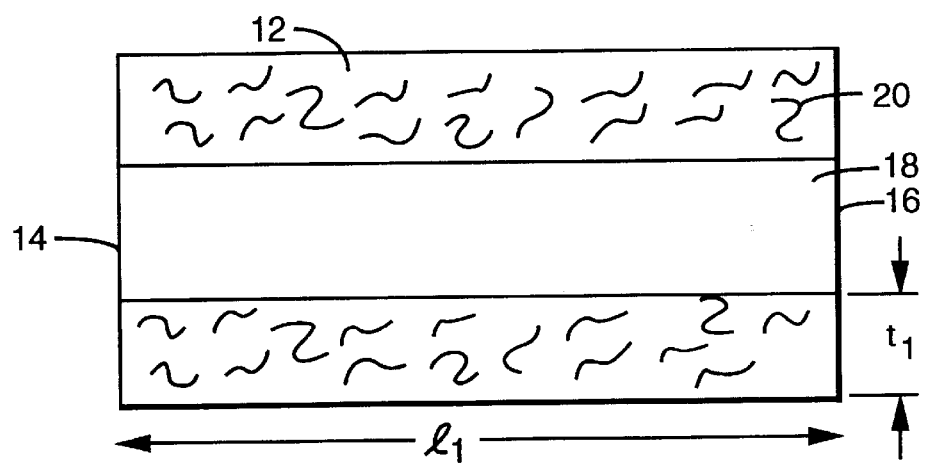
FIG. 1C illustrates a cross-section taken along line 1C—1C of FIG. 1B.

Referring now to the drawings, wherein similar parts are identified by like reference numerals, FIGS. 1A and 1B–1C illustrate prospective and cross-sectional views, respectively, of an implantable device 10. Implantable device 10 includes a body 12 having a first end 14 and an opposing second end 16. A central hollow bore 18 extends longitudinally through body 12 from first end 14 to second end 16, giving body 12 a thickness t1. Implantable device 10 can have any suitable length l1. The values of length l1 and thickness t1 depend, for example, on the procedure for which implantable device 10 is used.

Implantable device 10 contains a plurality of interstices 20, which cause body 12 to have a generally permeable characteristic. Body 12 can be made from any suitable material including, but not limited to, highly open-pored materials such as polymers of expanded polytetrafluoroethylene (ePTFE) and polyethylene terephthalate (PET).

In an alternative embodiment, body 12 is made from a less porous material, such as, but not limited to, polyurethanes, absorbable polymers, and combinations or variations thereof. Polyurethanes from which implantable device 10 may be made include, but are not limited to, Biomer, Biospan, and Elastion. Absorbable polymers from which implantable device 10 may be made include, but are not limited to, polycaprolactone (PCL), poly(lactic acid) (PLA), poly(glycolic acid) (PGA), polyanhydrides, polyorthoesters, polyphosphazenes, and components of extracellular matrix (ECM). In such an embodiment, additional interstices 20 can be formed in body 12 by any conventional methods known to one of ordinary skill in the art, including exposure of body 12 to a laser discharge to form a network of pores.

Figure 2A:
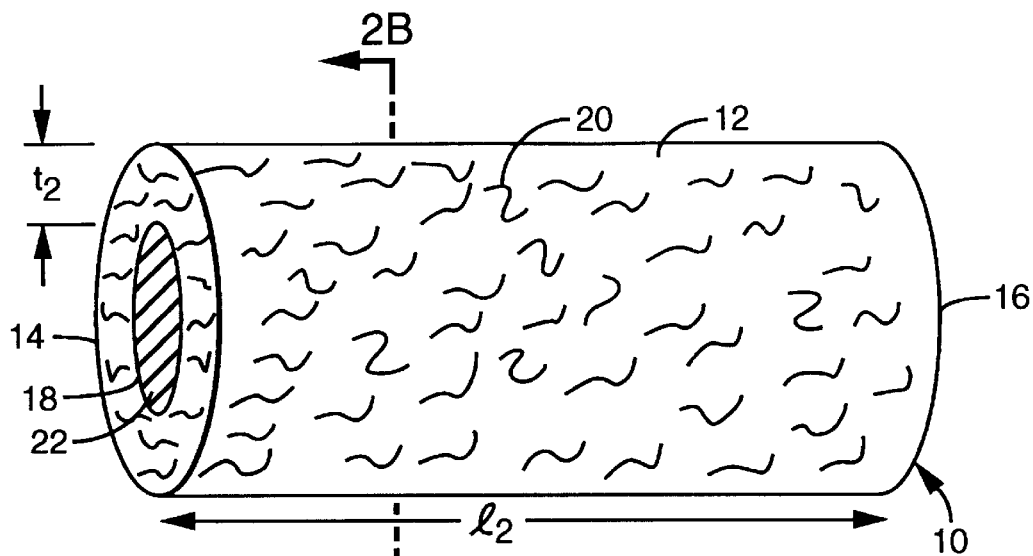
FIG. 2A illustrates a perspective view of the implantable device of FIG. 1, wherein a stent is within the central hollow bore of the implantable device.
Figure 2B:
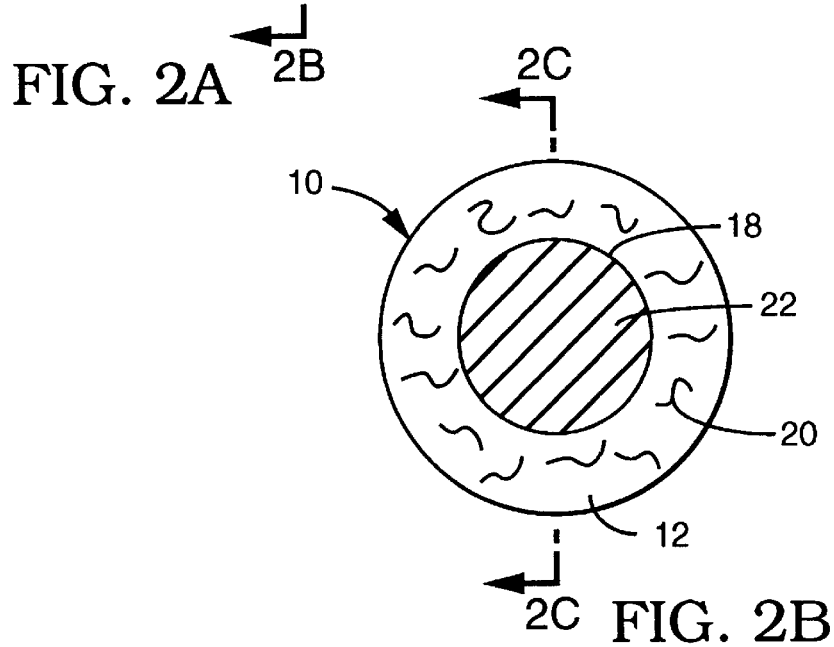
FIG. 2B illustrates a cross-section taken along line 2B—2B of FIG. 2A.
Figure 2C:
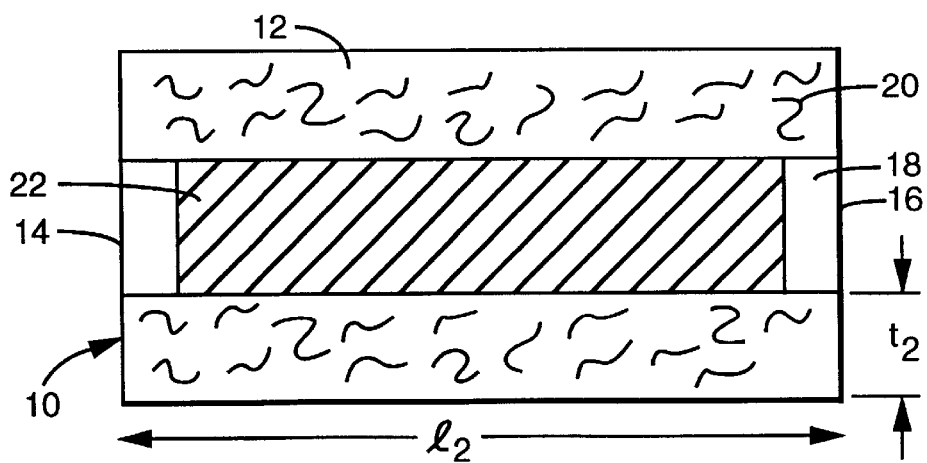
FIG. 2C illustrates a cross-section taken along line 2C—2C of FIG. 2B.

In one embodiment of the present invention, implantable device 10 of FIGS. 1A, 1B, and 1C is a vascular graft. In an alternative embodiment, illustrated in FIGS. 2A, 2B, and 2C, implantable device 10 is a covering for a prosthesis 22, which may be, for example, a self-expandable stent or a balloon-expandable stent. In such an embodiment, implantable device 10 is placed over all or part of the longitudinal outer surface of prosthesis 22 such that prosthesis 22 is at least partially within central hollow bore 18 of implantable device 10. The thickness t2 of the implantable device 10 of FIG. 2A for such an embodiment should not hinder the functionality of prosthesis 22, for example, the ability of prosthesis 22 to be radially expanded to a significantly rigid structure to maintain the patency of a vessel. Thickness t2 can be, for example, in the range of about 50 microns to about 500 microns, depending on the application. Additionally, the material from which implantable device 10 is made should have enough elasticity so as to allow prosthesis 22 to be expanded from a collapsed configuration to an expanded configuration. Body 12 of FIG. 2A can have any suitable length 12, depending on the application.

Figure 3A:
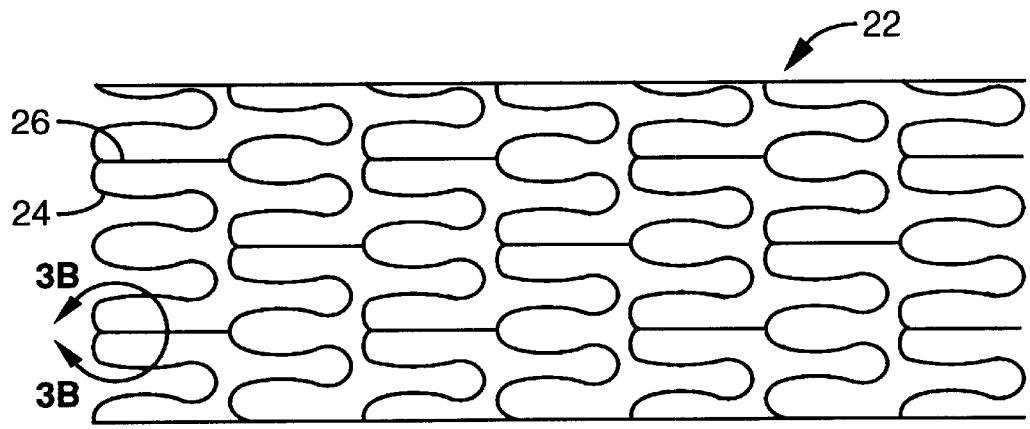
FIG. 3A is a side view of a conventional intraluminal prosthesis, the body of the prosthesis being defined by thread elements engaged to one another by connecting elements.

Prosthesis 22 may be any prosthesis so long as prosthesis 22 is capable of securely receiving the covering. The underlying structure of prosthesis 22 can be virtually of any design. For example, prosthesis 22 may be an expandable stent having a plurality of thread elements 24 that are interconnected by connecting elements 26 that are disposed between adjacent thread elements 24, as shown in FIG. 3A. Although thread elements 24 are illustratively shown in the form of cylinders or rings connected axially-displaced in parallel, other configurations, such as helices, coils, or braids, and other connections may be utilized.

Prosthesis 22 can be made of a metallic material or an alloy such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Prosthesis 22 also may be made from bioabsorbable or biostable polymers.

In some embodiments, prosthesis 22 may include a single depot, or a plurality of depots, formed in an outer surface thereof The depots may be filled, fully or partially, with a material as discussed below.

Figure 3B:
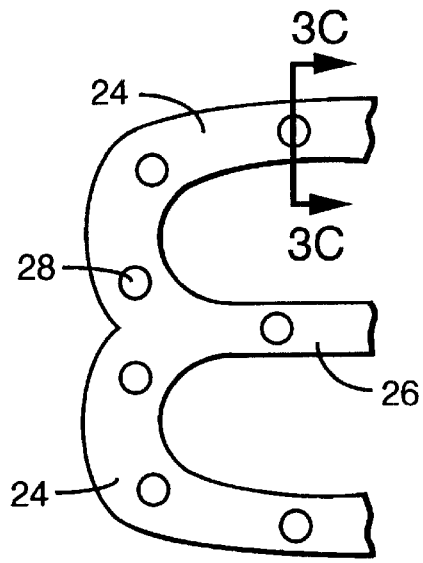
FIG. 3B is an enlarged view of section 3B of FIG. 3A, illustrating a portion of the thread elements and connecting elements and having depots formed therein.
Figure 3C:
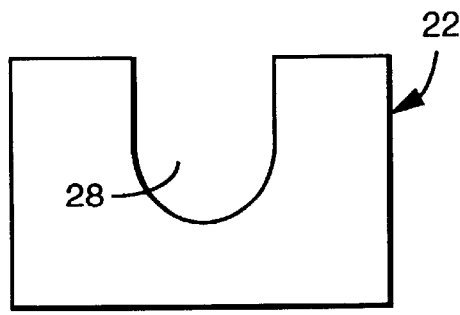
FIG. 3C is a cross-sectional view of the thread element, taken in the direction of the arrows and along the plane of line 3C—3C of FIG. 3B, illustrating a depot formed in the prosthesis in accordance with the various disclosed embodiments.
Figure 3D:
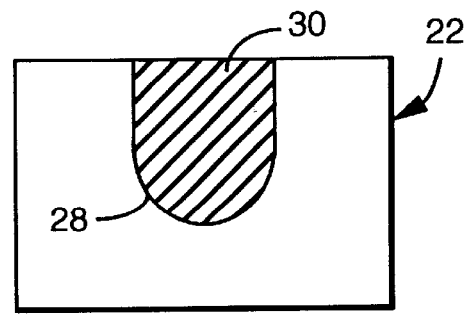
FIG. 3D illustrates the thread element of FIG. 3C in which a material has been deposited into the depot.

FIGS. 3B, 3C, and 3D illustrate a portion of thread elements 24 and connecting elements 26 of an exemplary prosthesis 22 having depots 28 formed in an outer surface thereof. Depots 28 can be formed in virtually any prosthesis 22 structure. Depots 28 are formed by a manufacturer at any preselected location and have any preselected depth, size, and geometrical configuration. The location of depot 28 within prosthesis 22 varies according to intended usage and application. The depth and size of depot 28 typically depend on the material and dimensions of prosthesis 22 and the type and amount of materials deposited within depot 28 as well as on the clinical purpose and usage of prosthesis 22. The depth and size of the individual depots 28 formed on a single prosthesis 22 can vary relative to one another. Depots 28 may be formed in a variety of selected geometrical shapes including, but not limited to, generally cylindrical shapes, generally conical shapes, and elongated trenches.

Depot 28, which may also be referred to as a pore or a cavity, may be formed as a laser trench on prosthesis 22 by exposing the surface to an energy discharge from a laser, such as an excimer laser. Alternative methods of forming such depots 28 include, but are not limited to, physical and chemical etching techniques. Techniques of laser fabrication or etching to form depots are well-known to one of ordinary skill in the art.

In some embodiments, depots 28 contain a material 30, as depicted in FIG. 3D. Depots 28 may contain a material that is the same, or different than the material impregnated in the covering as described below.

In some examples, the deposited material 30 is a therapeutic substance or agent such as, but not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

In other examples, the therapeutic substance in depots 28 is a radioactive isotope for prosthesis usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$).

In still other examples, material 30 is a radiopaque substance, such as gold, that is deposited into depots 28.

In other examples, deposited material 30 is a polymeric material. The polymeric material may be impregnated with a therapeutic substance. The polymeric material is most suitably bio-compatible, including polymers that are non-toxic, non-inflammatory, chemically inert, and substantially non-immunogenic in the applied amounts. The polymer is typically either bioabsorbable or biostable. A bioabsorbable polymer breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable materials include but are not limited to polycaprolactone (PCL), poly-D, L-lactic acid (DL-PLA), poly-L-lactic acid (L-PLA), poly(lactide-co-glycolide), poly (hydroxybutyrate), poly(hydroxybutyrate-co-valerate), polydioxanone, polyorthoester, polyanhydride, poly (glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene®, Parylast®, polyurethane (for example, segmented polyurethanes such as Biospan®), polyethylene, polyethlyene teraphthalate, ethylene vinyl acetate, silicone and polyethylene oxide.

Material 30 may be deposited into depots 28 using any suitable method. In an exemplary method of depositing material 30 into depots 28, material 30 is added to a first solvent. Material 30 is dispersed throughout the first solvent so that material 30 is in a true solution, saturated or supersaturated with the first solvent or suspended in fine particles in the first solvent. The first solvent can be virtually any solvent that is compatible with material 30. A high capillary permeation and a viscosity not greater than about ten centipoise allows the first solvent to penetrate into depots 28 more quickly, eliminating a requirement to apply the first solvent to prosthesis 22 for a prolonged period of time. Examples of suitable first solvents include, but are not limited to, acetone, ethanol, methanol, isopropanol, tetrahydrofuran, and ethyl acetate. The first solvent containing material 30 is applied to prosthesis 22, for example by immersing or spraying the solvent using procedures that are well-known to one having ordinary skill in the art. The first solvent containing material 30 is applied for a predetermined period of time, the specific time depending on the capillary permeation and viscosity of the first solvent, the volume of depots 28, and the amount of material 30 to be deposited.

After applying the first solvent containing material 30 for a selected duration, the first solvent is removed from the prosthesis using conventional techniques, such as evaporation in ambient pressure, room temperature and anhydrous atmosphere and/or by exposure to mild heat (e.g., 60° C.) under vacuum condition. Prosthesis 22 typically has a clustered or gross formation of material 30 gathered on the body surface. The cluster is generally removed by immersing prosthesis 22 in a non-solvent and agitating prosthesis 22 via mechanical perturbation techniques, such as vortexing or vigorous shaking. The non-solvent can have a low capillary permeation or a contact angle greater than about 90° and a viscosity not less than about 0.5 centipoise so that the second fluid is not capable of significantly penetrating into depots 28 during the process of agitation. Examples of a suitable non-solvent include, but are not limited to, saturated hydrocarbons or alkanes, such as hexane, heptane, and octane.

Prosthesis 22 is rinsed in a second solvent to facilitate dissolution of material 30. The second solvent generally has a low capillary permeation and a viscosity of not less than about 1.0 centipoise and is therefore incapable of significantly penetrating into depots 28 during the rinsing stage. The rinsing is conducted rapidly for example in a range from 1 second to about 15 seconds, the exact duration depending on the solubility of material 30 in the second solvent. Extended duration of exposure of prosthesis 22 to the second solvent may lead to the penetration of the second solvent into depots 28. The rinsing step is repeated, if desired, until all traces of material 30 are removed from the surface of prosthesis 22. The second solvent removes excess material 30 from the surface of the prosthesis body. Useful examples of second solvents include, but are not limited to, dimethylsulfoxide (DMSO), water, DMSO in an aqueous solution, glyme, and glycerol. The second solvent is removed from the prosthesis body using conventional techniques. The first and second solvents as well as the non-solvent are selected to not adversely affect the characteristics and composition of material 30. Although one method of depositing material 30 into depots 28 has been described here, depots 28 may be filled using any suitable method.

Below, methods are disclosed that allow substances, such as solids or hydrogels, to be deposited or formed, respectively, within the above-described implantable device 10. The methods may be used in applications where implantable device 10 is a vascular graft or a covering for a prosthesis 22, among other possibilities.

Deposition of a Solid

Figure 4A:
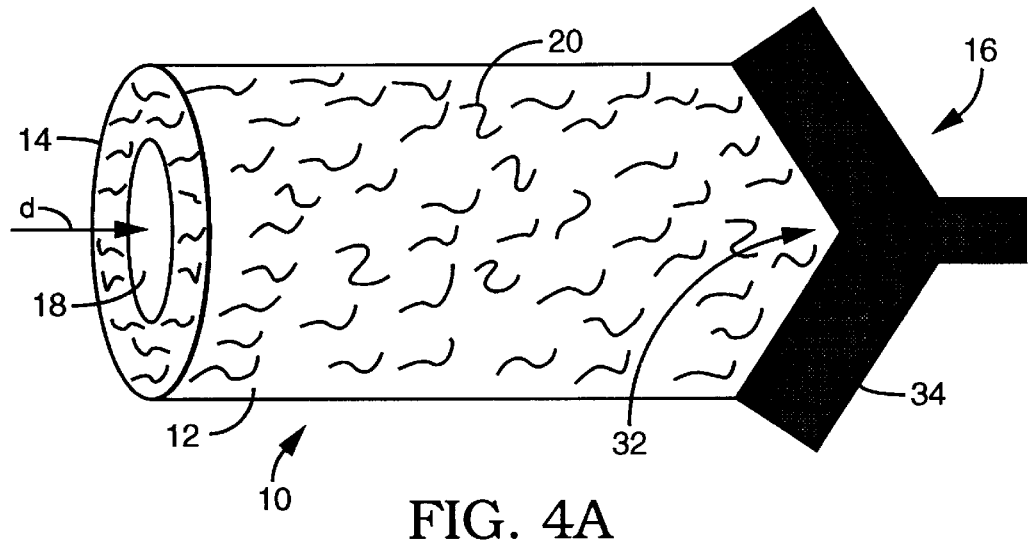
FIG. 4A illustrates the application of a fluid to an implantable device in accordance with the various disclosed embodiments.

In preparation for the application of a solid within implantable device 10, a blockage 32 is caused at second end 16 of implantable device 10 such that fluid cannot significantly pass through second end 16 of implantable device 10, as illustrated in FIG. 4A. Blockage 32 may be created by physically blocking second end 16 of implantable device 10, for example, by clamping second end 16 with a clamp 34 or some other device, such as a paper clip or tweezers. In embodiments in which implantable device 10 is a covering that is disposed over prosthesis 22, second end 16 of the covering should extend beyond prosthesis 22 to allow a user to clamp second end 16 of the covering without also clamping prosthesis 22. It is contemplated that other methods of blocking second end 16 can be employed, and the application of the embodiments of the invention is not limited to the type of blocking means employed.

Figure 4B:
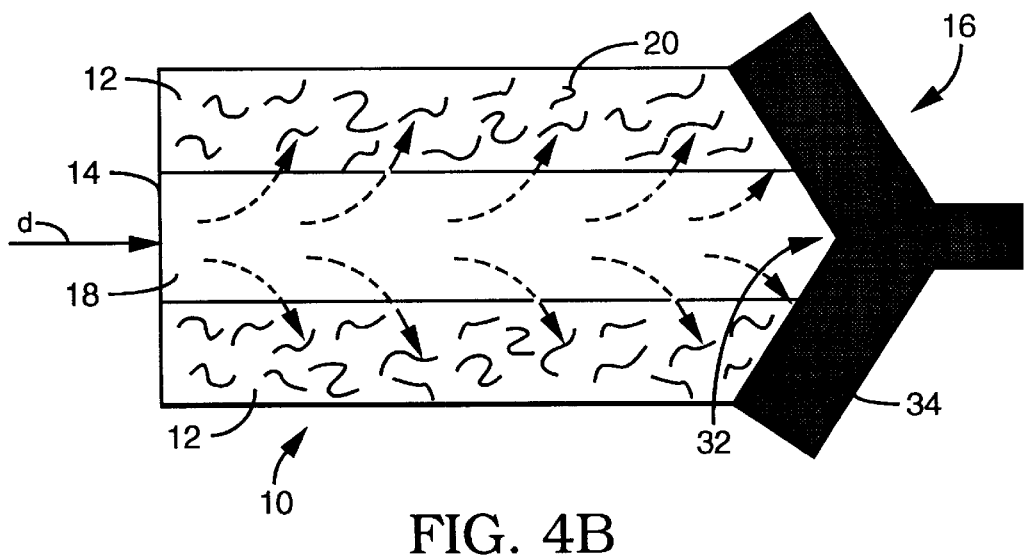
FIG. 4B illustrates a cross-sectional view of the implantable device of FIG. 4A as a fluid penetrates into interstices thereof in accordance with the various disclosed embodiments.

Using a syringe or similar instrument, a composition may be introduced into bore 18 of implantable device 10 at first end 14 in a direction d. The composition should be delivered in a controlled manner and at a controlled pressure to allow the composition to penetrate into and pass through interstices 20. The pressure can be any suitable pressure necessary to achieve a flow rate in the range of about 0.1 mL/min to about 2 mL/min so long as the pressure does not exceed the burst pressure of the material of body 12. The pressure at which the composition is introduced into bore 18 should not adversely affect the structure of body 12 so as to cause defects, such as cavities or crests, in the inner or outer surfaces of body 12. Additionally, the pressure at which the composition is introduced should not disrupt blockage 32 at second end 16. Unable to pass through blockage 32 at second end 16 of implantable device 10, the composition is forced through body 12, as depicted in FIG. 4B, thereby penetrating into interstices 20. Once the composition has completely filled interstices 20, any excess composition may seep out through the surface of implantable device 10, interstices 20 remaining filled with the composition.

The composition includes a solid and a first fluid. The solid should be in true solution, saturated, super-saturated, or suspended as fine particles in the first fluid. In some embodiments, the solid may be a hydrophobic, bioerodable polymer, organic-soluble heparin, or organic-soluble phosphorylcholine. Exemplary hydrophobic, bioerodable polymers include, but are not limited to, polycaprolactone (PCL), poly(lactic acid) (PLA), poly(glycolic acid) (PGA), polyanhydrides, polyorthoesters, and polyphosphazenes.

Figure 5A:
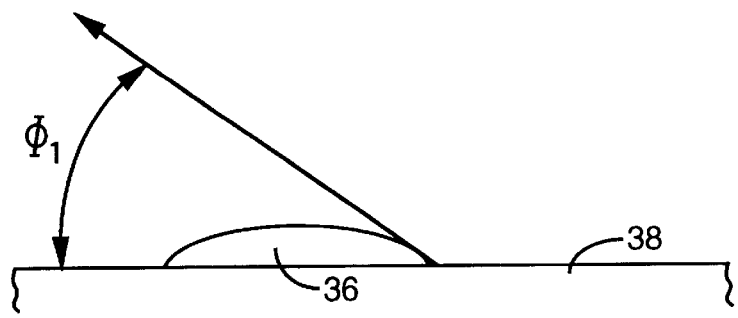
FIG. 5A illustrates a fluid on a solid substrate having a contact angle □1.
Figure 5B:
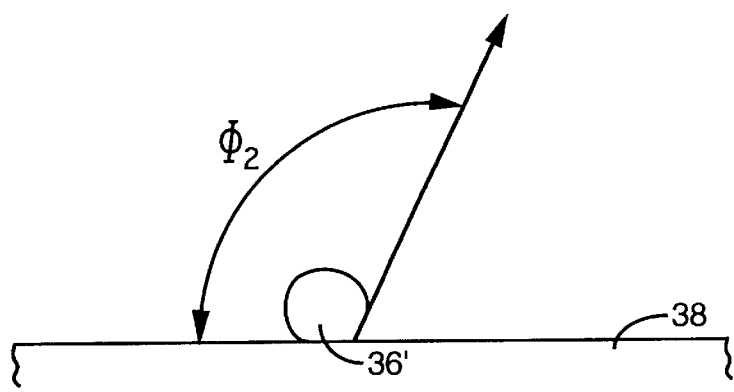
FIG. 5B illustrates a fluid on a solid substrate having a contact angle □2.

In such embodiments, the first fluid can have a viscosity from about 0.2 to about 10 centipoise, or more particularly, from about 0.4 to about 0.6 centipoise, such that the first fluid may readily penetrate into interstices 20. In addition, the first fluid should have a high capillary permeation. Capillary permeation, or wetting, is the movement of fluid on a solid substrate driven by interfacial energetics. Capillary permeation is quantitated by a contact angle, which is defined as the angle at the tangent of the first solvent droplet in fluid phase that has taken an equilibrium shape on a solid surface. FIG. 5A illustrates a fluid droplet 36 on a solid substrate 38. Fluid droplet 36 has a contact angle $\Phi_1$, which is less than 90°. In contrast, FIG. 5B illustrates a fluid droplet 36' having a contact angle $\Phi_2$, which is greater than 90°. A low contact angle, as depicted in FIG. 5A, indicates a higher wetting liquid; a high contact angle, as depicted in FIG. 5B, indicates a lower wetting liquid. Since wetting of the material of which implantable device 10 is made is an essential part of the present invention, higher wetting liquids are preferred. Thus, in the embodiments described above, a first fluid should have a contact angle not more than 90°.

Exemplary first fluids include, but are not limited to, tetrahydrofuran (THF), dimethylformamide (DMF), dimethyl sulfoxide (DMSO), acetone, freon, hexafluoroisopropanol (HFIP), chloroform, 1,1,2-trichloroethane, and combinations thereof. The particular first fluid selected depends on the particular solid applied to implantable device 10 as well as on the material of which implantable device 10 is made. For example, if implantable device 10 is made of an absorbable polymer, caution should be exercised in the selection of all fluids since some absorbable polymers of which an implantable device 10 can be made dissolve in fluids that are otherwise suitable for usage in the present invention.

In one example, the composition can include organic-soluble heparin and a first fluid selected from freon, tetrahydrofuran (THF), and dimethylformamide (DMF).

In another example, the composition can include organic-soluble phosphorylcholine and a first fluid selected from acetone and freon.

In yet another example, the composition can include polycaprolactone (PCL) and acetone as the solid and first fluid, respectively.

In another example, the composition can include poly(lactic acid) (PLA) and a first fluid selected from hexafluoroisopropanol (HFIP), chloroform, and 1,1,2-trichloroethane.

In still another example, the composition can include poly(glycolic acid) (PGA) and hexafluoroisopropanol (HFIP) as the solid and first fluid, respectively.

In another example, the composition can include a polyanhydride and a first fluid selected from tetrahydrofuran (THF) and dimethyl sulfoxide (DMSO).

In yet another example, the composition can include a polyorthoester and a first fluid selected from chloroform, methylene chloride, and dioxane.

In still another example, the composition can include a polyphosphazene and a first fluid selected from tetrahydrofuran (THF) and dimethylformamide (DMF).

The application of the composition is followed by the removal of the first fluid from implantable device 10. The first fluid may be removed from implantable device 10 using techniques such as evaporation at ambient pressure and room temperature in an anhydrous atmosphere for 48 hours, or exposure to mild heat, e.g., 60–65° C., under vacuum conditions. In examples wherein implantable device 10 is made of an absorbable polymer, the first fluid should be removed relatively quickly to avoid prolonged solvent exposure and thereby ensure the mechanical integrity of the absorbable implantable device 10. Upon removal of essentially all of the first fluid, the solid remains within interstices 20 of implantable device 10.

In alternative embodiments, another fluid or a plurality of other fluids are applied to implantable device 10 prior to, and in the same manner as, the application of the composition described above. For example, in some embodiments, a second fluid is applied to implantable device 10 prior to the application of the composition. Unable to pass through blockage 32 at second end 16 of implantable device 10, the second fluid is forced through body 12, as depicted in FIG. 4B, thereby penetrating into interstices 20.

In such embodiments, the second fluid should have a high capillary permeation, as defined above, and thus, the second fluid should have a contact angle not more than 90°. The second fluid can also have a viscosity from about 0.2 to about 10 centipoise, or more particularly from about 0.4 to about 0.6 centipoise, such that the second fluid may penetrate into interstices 20. Such second fluids depend on the particular solid applied to implantable device 10 as well as on the material of which implantable device 10 is made and may include, but are not limited to, acetone, isopropanol, ethanol, freon or combinations thereof.

In embodiments in which the second fluid is miscible with the first fluid contained in the composition, application of the composition as described above following the application of the second fluid causes the composition to mix with the second fluid already within interstices 20. As the composition is applied to implantable device 10, the composition increasingly dilutes, and finally significantly replaces, the second fluid within interstices 20. Traces or residues of the second fluid may remain in interstices 20.

In other embodiments in which the second fluid is not miscible with the first fluid contained in the composition, a third fluid can be applied to implantable device 10 subsequent to the application of the second fluid and prior to the application of the composition in the manner described above. The third fluid should be miscible with both the first and third fluids.

In one embodiment where the second fluid is not miscible with the first fluid contained in the composition, the third fluid is miscible with both the first and second fluids. As the third fluid penetrates into interstices 20, the third fluid mixes with the second fluid already within interstices 20. As the third fluid is applied to implantable device 10, the third fluid increasingly dilutes, and finally significantly replaces, the second fluid within interstices 20. Similarly, as the composition penetrates into interstices 20, the first fluid mixes with, increasingly dilutes, and finally significantly replaces, the third fluid within interstices 20.

In one embodiment where the second fluid is not miscible with the first fluid contained in the composition, the third fluid is miscible with the first fluid but is not miscible with the second fluid. In such an embodiment, a fourth fluid which is miscible with both the second and third fluids can be applied to implantable device 10 in the manner described above. The fourth fluid can be introduced after the introduction of the second fluid and prior to the introduction of the third fluid. Alternatively, the fourth fluid can be added to and introduced simultaneously with either the second fluid or the third fluid. For example, if freon is selected as the second fluid and water is selected as the third fluid, a fourth fluid of acetone or n-propanol is a suitable bridging fluid between the immiscible second and third fluids.

In another embodiment where the second fluid is not miscible with the first fluid contained in the composition, the third fluid is miscible with the second fluid but is not miscible with the first fluid. In such an embodiment, a fourth fluid which is miscible with both the first and third fluids can be applied to implantable device 10 in the manner described above. The fourth fluid acts as a bridging fluid between the immiscible first and third fluids and can be introduced after the introduction of the third fluid and prior to the introduction of the composition or simultaneously with either the third fluid or the composition.

In still another embodiment where the second fluid is not miscible with the first fluid contained in the composition, the third fluid is not miscible with the first fluid nor with the second fluid. In such an embodiment, a more suitable third fluid should be selected. Alternatively, bridging fluids applied between the second and third fluids and between the third fluid and the composition may be applied in the manner described above.

In another embodiment of the present invention, second and third fluids which are miscible with one another as well as with the first fluid contained in composition 10 are successively applied to implantable device 10 prior to, and in the same manner as, the application of composition 10 described above. In such an embodiment, the second fluid is applied to implantable device 10. After the second fluid penetrates into interstices 20, the third fluid is applied. The third fluid mixes with, increasingly dilutes, and finally significantly replaces, the second fluid already within interstices 20. The composition is then applied to implantable device 10. As the composition penetrates into interstices 20, the composition mixes with, increasingly dilutes, and finally significantly replaces, the third fluid within interstices 20.

In the above-described embodiments in which another fluid or a plurality of other fluids are applied to implantable device 10 prior to the application of the composition, exemplary solids include, but are not limited to, hydrophilic, bioerodable polymers as well as components of extracellular matrix (ECM). Examples of hydrophilic, bioerodable polymers include, but are not limited to, polyethylene glycol (PEG), polyvinylpyrrolidone (PVP), hyaluronic acid, pluronic, water-soluble chitin, polyacrylamide, polyalginate, heparin, and water-soluble phosphorylcholine. Examples of components of extracellular matrix (ECM) include, but are not limited to, collagen, elastin, laminin, and glycosaminoglycan.

The concentration of the solid in the composition is selected such that the solution viscosity is low enough to allow penetration into interstices 20 and high enough to allow a sufficient amount of solid to be deposited upon drying. For example, the concentration of polyethylene glycol (PEG), polyvinylpyrrolidone (PVP), pluronic, or polyacrylamide in the composition should be about 15–30% by weight of the total weight of the composition, the concentration of water-soluble chitin in the composition should be about 10–15% by weight of the total weight of the composition, and the concentration of hyaluronic acid in the composition should be no more than about 2% by weight of the total weight of the composition.

In one set of examples, the solid included in the composition, and therefore applied into implantable device 10, can be polyethylene glycol (PEG), polyvinylpyrrolidone (PVP), hyaluronic acid, pluronic, water-soluble chitin, polyacrylamide, polyalginate, or water-soluble phosphorylcholine. In such examples, the first fluid can be water and the second fluid can be acetone, isopropanol, ethanol or freon. The third fluid can be water. However, when the solid employed is polyethylene glycol (PEG), polyvinylpyrrolidone (PVP), or pluronic, the third fluid may alternatively be dimethyl sulfoxide (DMSO).

In another set of examples, the solid included in the composition, and thus applied into implantable device 10, is heparin, the second fluid can be acetone, isopropanol, or ethanol, and both the first and third fluids can be water.

In still another set of examples, the solid included in the composition, and therefore applied into implantable device 10, can be a component of extracellular matrix. Representative examples include collagen, elastin, laminin, and glycosaminoglycan. In such examples, the second fluid can be acetone, isopropanol, or ethanol, and both the first and third fluids can be water.

In some embodiments of the above-disclosed method, the composition contains a therapeutic substance. The therapeutic substance can make up from about 0.1% to about 20%, or more particularly from about 1% to about 10%, by weight of the total weight of the composition. After a composition containing a therapeutic substance is applied to implantable device 10 and implantable device 10 is dried, both the solid and the therapeutic substance remain within interstices 20 of implantable device 10.

Therapeutic substances or agents may include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of such therapeutic substances were listed above in association with the discussion of material 30 which may be deposited into depots 28 formed within prosthesis 22, and such examples are equally applicable here. While the foregoing therapeutic substances or agents are well-known for preventative and treatment properties, the substances or agents are provided by way of example and are not meant to be limiting. Other therapeutic substances are equally applicable for use with the disclosed methods and compositions.

Formation of a Hydrogel

In preparation for the application of a hydrogel within implantable device 10, blockage 32 is caused at second end 16 of implantable device 10, as illustrated in FIG. 4A and described above. A composition is then introduced into implantable device 10 and forced through body 12, as depicted in FIG. 4B and described above, thereby penetrating into interstices 20.

The composition includes at least one crosslinkable pre-polymer and a first fluid in which the pre-polymer is soluble. The pre-polymer should be in true solution, saturated, or super-saturated in the first fluid. Exemplary crosslinkable pre-polymers include, but are not limited to, polyethylene glycol (PEG) diacrylate, unsaturated hyaluronic acid, and pluronic. The concentration of pre-polymer in the composition is selected such that the solution viscosity is low enough to allow penetration into interstices 20 but still high enough to ensure effective crosslinking of the pre-polymer since a solution too dilute does not form a crosslinked hydrogel. For example, the concentration of PEG diacrylate in the composition should be about 15–30% by weight. The composition may also contain a photoinitiator if the crosslinkable pre-polymer is to be crosslinked using light energy.

The application of the composition is followed by crosslinking the crosslinkable prepolymer within the composition that has penetrated interstices 20. A snug-fit mandrel is placed within bore 18 of implantable device 10, and the pre-polymer within the composition is cured to form a hydrogel within interstices 20 of implantable device 10. Curing may be accomplished photochemically using ultraviolet or visible irradiation and a photoinitiator, thermally, or by moisture curing at room temperature. The practice of these and other suitable curing procedures is well known to one of ordinary skill in the art.

In some embodiments, the crosslinkable pre-polymer is crosslinked internally upon curing. That is, a pre-polymer molecule is crosslinked with another molecule of the same pre-polymer rather than to another substance. Examples of crosslinkable pre-polymers that may be internally crosslinked include, but are not limited to, PEG diacrylate, unsaturated hyaluronic acid, pluronic and absorbable PEG diacrylate hydrogel precursors.

In other embodiments, the crosslinkable pre-polymer is crosslinked with another substance. For example, a crosslinkable pre-polymer, such as PEG diacrylate, may be crosslinked with an unsaturated monomer. Examples of suitable unsaturated monomers include, but are not limited to, vinyl pyrrolidone, acrylamide, phosphorylcholine, acrylic acid, dimethyl aminoethyl methacrylate (DMAMA), vinyl pyridine, trans-amidated acrylamide, methacrylic acid, and vinyl phosphonic acid. The unsaturated monomer may be selected for the particular functional group that is contained within the monomer and is donated to the hydrogel that is formed upon crosslinking the unsaturated monomer with a crosslinkable pre-polymer.

Following the crosslinking of the pre-polymer within the pre-polymer solution, any remaining amounts of the first fluid injected therewith may be removed from implantable device 10. The first fluid may be removed using drying techniques described above. Upon removal of the first fluid substantially to elimination, the hydrogel remains within body 12 of implantable device 10.

In alternative embodiments, another fluid or a plurality of other fluids are applied to implantable device 10 prior to the application of the composition and the subsequent crosslinking of the pre-polymer. These embodiments may employ a second fluid, a third fluid, a bridging fluid, or a combination thereof. The use of such fluids and the methods associated therewith were described above in reference to the deposition of a solid within implantable device 10, and the above discussion is equally applicable here in reference to the formation of a hydrogel within implantable device 10.

In one particular set of examples in which a plurality of fluids are employed, the crosslinkable pre-polymer is PEG diacrylate, unsaturated hyaluronic acid, or pluronic. In such examples, the second fluid can be acetone, isopropanol, ethanol, or freon, and both the first and third fluids can be water. In examples with freon as the second fluid, a fourth fluid of either acetone or n-propanol is applied to implantable device 10 after the application of freon and prior to the application of the third fluid, e.g., water. In examples with PEG-diacrylate or unsaturated hyaluronic acid selected as the pre-polymer, the resulting hydrogel is not bioerodable. In contrast, in examples where the pre-polymer selected is pluronic, the resulting hydrogel is bioerodable.

Figure 6:
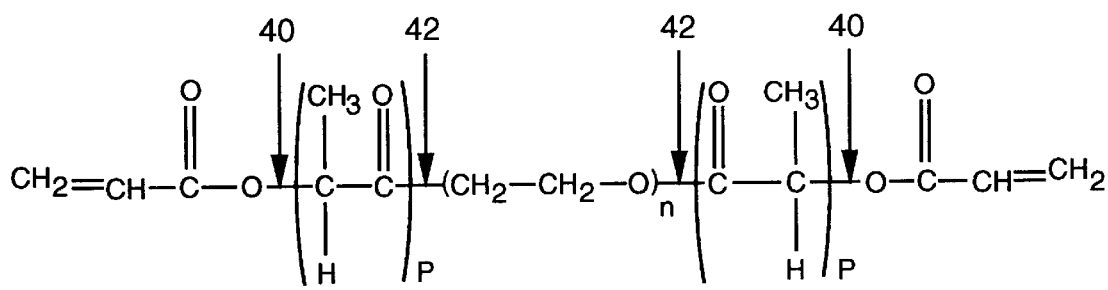
FIG. 6 illustrates the chemical structure of PEG diacrylate end-capped with lactide.

In another example in which a plurality of fluids are employed, the crosslinkable pre-polymer is an absorbable PEG diacrylate hydrogel precursor, such as a PEG diacrylate that is end-capped with lactide, as shown in FIG. 6. The second fluid can be acetone, isopropanol, ethanol, or freon, and both the first and third fluids can be water. If the second fluid is freon, a bridging fluid of either acetone or n-propanol is employed between the immiscible second and third fluids as described above. Upon curing, the end-capped PEG diacrylate forms a transient hydrogel, since over time the hydrogel will be cleaved at the bonds 40 and 42 of FIG. 6 and is thus wholly bioerodable. A transient hydrogel is particularly suited for incorporation into absorbable implantable devices 10.

In some embodiments of the disclosed method, the composition additionally contains a therapeutic substance. The therapeutic substance can make up from about 0.1% to about 20%, or more particularly from about 1% to about 10%, by weight of the total weight of the composition. After a composition containing a therapeutic substance is applied to implantable device 10 and crosslinked, both the resulting hydrogel and the therapeutic substance remain within interstices 20 of implantable device 10.

Therapeutic substances or agents may include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of such therapeutic substances were listed above in association with the discussion of material 30 which may be deposited into depots 28 formed within prosthesis 22, and such examples are equally applicable here. While the foregoing therapeutic substances or agents are well-known for preventative and treatment properties, the substances or agents are provided by way of example and are not meant to be limiting. Other therapeutic substances are equally applicable for use with the disclosed methods and compositions.

In one set of examples where the composition includes a therapeutic substance, an unsaturated monomer may be selected for inclusion in the composition based on electrical charge so as to control the release rate of a therapeutic substance from a hydrogel formed within implantable device 10. In one such example, the composition includes PEG diacrylate, a positively-charged unsaturated monomer, and a negatively-charged therapeutic substance such as heparin. Representative examples of positively-charged unsaturated monomers include, but are not limited to, dimethyl aminoethyl methacrylate (DMAMA), vinyl pyridine, and trans-amidated acrylamide. PEG diacrylate is cross-linked with the positively-charged unsaturated monomer, thereby forming a positively charged hydrogel containing the negatively-charged therapeutic substance. Since the hydrogel and the therapeutic substance have opposing charges and thus are attracted to one another, the rate at which the therapeutic substance is released from the hydrogel within implantable device 10 after implantation is decreased.

Conversely, in an example in which PEG diacrylate is crosslinked with a negatively-charged unsaturated monomer, thereby forming a negatively-charged hydrogel, the release rate of a negatively-charged therapeutic substance from the negatively-charged hydrogel within implantable device 10 is increased, since the negative charges on both the hydrogel and the therapeutic substance repel one another. Representative examples of negatively-charged unsaturated monomers include, but are not limited to, acrylic acid, methacrylic acid and vinyl phosphonic acid.

Methods of Use

An implanted vascular graft or covered stent, having the above-described solid or hydrogel incorporated within interstices throughout, is useful for treating occluded regions of blood vessels caused by thrombosis and/or restenosis, among other possible uses.

Vascular grafts may be used to replace, bypass, or reinforce diseased or damaged sections of a vein or artery. The general procedure for implantation includes the step of pre-clotting, wherein the graft is immersed in the blood of the patient and allowed to stand for a period of time sufficient for clotting to ensue. After pre-clotting, hemorrhaging is less likely to occur when the graft is implanted and thus the growth of tissue is not impeded. Grafts may be placed either through invasive surgery or non-invasively through percutaneous endoluminal transport. Percutaneous delivery of a graft avoids the complications and risks of surgery. The graft may be attached to the vessel at each end of the diseased region, thus bypassing the diseased region. Alternatively, the diseased region may be removed and replaced by the graft.

Covered stents may be placed in a wide array of blood vessels, both arteries and veins. Briefly, an angiography is first performed to determine the appropriate positioning for stent therapy. Angiography is typically accomplished by using a catheter to inject a radiopaque contrasting agent into an artery or vein as an X-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein and advanced into the appropriate blood vessel by steering the catheter through the vascular system under fluoroscopic guidance. A stent having the above described covering may then be expanded at the desired area of treatment. A post-insertion angiogram may also be utilized to confirm appropriate positioning.

EXAMPLES

Exemplary embodiments of the invention are illustrated below. These examples are being given by way of illustration only and not by way of limitation. The parameters given, including, without limitation, percentages of prepolymer, solid, fluids, therapeutic substance, temperature, duration of time, and other data, are exemplary, not limiting.

Example 1

A PTFE vascular graft was closed at one end with a paper clip. Organic-soluble heparin was dissolved in freon such that organic-soluble heparin constituted about 5% by weight of the total weight of the solution. The organic-soluble heparin solution was permeated through the circumferential area of the graft by flushing the inner lumen twice with the organic-soluble heparin solution using a syringe. A mandrel was selected such that it snugly fit within the bore of the graft. The mandrel was placed within the bore of the graft, and the graft was dried in a vacuum oven at 60° C. for about 12 hours. The organic-soluble heparin remained within the interstices of the graft.

Example 2

A PTFE vascular graft is closed at one end with a paper clip. Acetone is permeated through the circumferential area of the graft by flushing the inner lumen with about 2 mL of acetone using a syringe. Next, deionized water is permeated through the circumferential area of the graft by flushing the inner lumen with about 2 mL of deionized water using a syringe. An aqueous solution of hyaluronic acid is made by stirring hyaluronic acid in deionized water on a hot plate at 50° C. for about 12 hours. The hyaluronic acid constitutes 0.5% by weight of the total weight of the solution. Following the deionized water flush, the hyaluronic acid solution is flushed twice through the inner lumen of the graft using a syringe. A mandrel is selected such that it snugly fits the within the bore of the graft. The mandrel is placed within the bore of the graft, and the graft is dried in a vacuum oven at 60° C. for about 12 hours. It is predicted that hyaluronic acid will remain within the interstices of the graft.

Example 3

A covered stent having a covering made of PTFE is closed at one end with a paper clip. Acetone is permeated through the circumferential area of the covering by flushing the inner lumen with about 2 mL of acetone using a syringe. A solution of PEG-di-isocyanate is made in benzene. The PEG-di-isocyanate constitutes 30% by weight of the total weight of the solution. Following the acetone flush, the PEG-di-isocyanate solution is flushed through the inner lumen of the covering using a syringe. The covering is dried under vacuum at room temperature for 2 hours. An aqueous solution of hyaluronic acid is made by stirring hyaluronic acid in deionized water on a hot plate at 50° C. for about 12 hours. The hyaluronic acid constitutes 0.5% by weight of the total weight of the solution. Following the drying step, the hyaluronic acid solution is flushed twice through the inner lumen of the covering using a syringe. A mandrel is selected such that it snugly fits within the bore of the covering. The mandrel is placed within the bore of the covering, and the covering is dried in a vacuum oven at 80° C. for about 24 hours. It is predicted that PEG-di-isocyanate and hyaluronic acid will remain within the interstices of the covering.

Example 4

A PTFE vascular graft is closed at one end with a paper clip. Acetone is permeated through the circumferential area of the graft by flushing the inner lumen with about 2 mL of acetone using a syringe. Next, deionized water is permeated through the circumferential area of the graft by flushing the inner lumen with about 2 mL of deionized water using a syringe. A three-component aqueous solution is made by dissolving hyaluronic acid, PEG-di-amine, and water soluble carbodiimide in deionized water and vortexing the solution for 2 minutes at room temperature. Hyaluronic acid constitutes 0.5% by weight of the total weight of the solution, PEG-di-amine constitutes 10% by weight of the total weight of the solution, and water soluble carbodiimide constitutes 2% by weight of the total weight of the solution. Following the deionized water flush, the solution is flushed twice through the inner lumen of the graft using a syringe. A mandrel is selected such that it snugly fits within the bore of the graft. The mandrel is placed within the bore of the graft, and the graft is dried in a vacuum oven at 30°C. for about 12 hours. It is predicted that hyaluronic acid and PEG-di-amine will remain within the interstices of the graft.

Example 5

A covered stent having a covering made of PTFE is closed at one end with a paper clip. Acetone is permeated through the circumferential area of the covering by flushing the inner lumen with about 2 mL of acetone using a syringe. A two-component aqueous solution is made by dissolving PEG-diacrylate and benzoyl peroxide in deionized water. PEG-diacrylate constitutes 40% by weight of the total weight of the solution and benzoyl peroxide constitutes 5% by weight of the total weight of the solution. Following the acetone flush, the solution is flushed twice through the inner lumen of the covering using a syringe. A mandrel is selected such that it snugly fits within the bore of the covering. The mandrel is placed within the bore of the covering, and the covering is dried in a vacuum oven at 80° C. for about 24 hours. It is predicted that PEG-diacrylate will remain within the interstices of the covering.

Example 6

A PTFE vascular graft is closed at one end with a paper clip. Acetone is permeated through the circumferential area of the graft by flushing the inner lumen with about 2 mL of acetone using a syringe. A three-component aqueous solution is made by dissolving PEG-diacrylate, hydroxy-ethyl-methacrylate (HEMA), and benzoyl peroxide in deionized water. PEG-diacrylate constitutes 40% by weight of the total weight of the solution, hydroxy-ethyl-methacrylate constitutes 10% by weight of the total weight of the solution, and benzoyl peroxide constitutes 5% by weight of the total weight of the solution. Following the acetone flush, the solution is flushed twice through the inner lumen of the graft using a syringe. A mandrel is selected such that it snugly fits within the bore of the graft. The mandrel is placed within the bore of the graft, and the graft is dried in a vacuum oven at 80° C. for about 24 hours. It is predicted that PEG-diacrylate and hydroxy-ethyl-methacrylate will form a water soluble gel with hydroxyl functionality for use in any secondary coupling application and will remain within the interstices of the graft.

Example 7

A PTFE vascular graft is closed at one end with a paper clip. Acetone is permeated through the circumferential area of the graft by flushing the inner lumen with about 2 mL of acetone using a syringe. Next, tetrahydrofuran (THF) is permeated through the circumferential area of the graft by flushing the inner lumen with about 2 mL of THF using a syringe. An ethylene vinyl alcohol (EVAL) solution is made such that ethylene vinyl alcohol constitutes 25% by weight of the total weight of the solution, dimethyl sulfoxide (DMSO) constitutes 50% by weight of the total weight of the solution, and tetrahydrofuran (THF) constitutes 25% by weight of the total weight of the solution. Following the deionized water flush, the solution is flushed twice through the inner lumen of the graft using a syringe. A mandrel is selected such that it snugly fits within the bore of the graft. The mandrel is placed within the bore of the graft, and the graft is dried in a vacuum oven at 60° C. for about 24 hours. It is predicted that EVAL will remain within the interstices of the graft.

While particular embodiments, applications, and examples of the present invention have been shown and described, it will be apparent to those of ordinary skill in the art that changes and modifications can be made without departing from this invention in its broader aspects. For example, fluids may be alternatively applied to implantable device 10 by successive immersion and removal of implantable device 10 from each fluid. This immersion method of application is particularly useful when implantable device 10 is a covering for a prosthesis 22, as such a covering is thin and thus easily permeated. Therefore, the appended claims are to encompass within their scope all such changes and modifications as fall within the true spirit and scope of this invention.

What is claimed is:

1. A method of impregnating an implantable device with a hydrogel, the method comprising:
   (a) applying a composition to an implantable body, said body having cavities disposed therein, such that said composition penetrates into said cavities, said composition comprising a pre-polymer and a fluid; and
   (b) causing said pre-polymer to crosslink to form a hydrogel within said cavities of said body.

2. The method of claim 1, wherein said implantable device is selected from the group consisting of stents, grafts and coverings adapted to be disposed over a prosthesis.

3. The method of claim 1, wherein said body is made from a material selected from the group consisting of expanded polytetrafluoroethylene (ePTFE), a polyethylene terephthalate (PET), polyurethanes (PU), an absorbable polymer, and combinations thereof.

4. The method of claim 1, wherein said body has a first end and an opposing second end and wherein a hollow bore extends longitudinally through said body from said first end to said second end.

5. The method of claim 4, further comprising inserting a prosthesis at least partially within said hollow bore of said body.

6. The method of claim 5, wherein said prosthesis is a stent.

7. The method of claim 4, wherein applying said composition to said body comprises:
   physically blocking said second end of said body such that fluid cannot significantly pass through said second end of said body; and
   introducing said composition into said bore at said first end, wherein said composition penetrates into said cavities.

8. The method of claim 1, wherein said fluid has a contact angle with the surface of said body of not more than 90°.

9. The method of claim 1, wherein said fluid has a viscosity of about 0.2 to about 10 centipoise at room temperature.

10. The method of claim 1, wherein said composition additionally includes organic-soluble heparin or phosphorylcholine.

11. The method of claim 1, wherein said composition additionally includes a therapeutic substance selected from the group consisting of antineoplastic, antiplatelet, anticoagulant, fibrinolytic, antimitotic, thrombin inhibitor, antiinflammatory, antiproliferative, antioxidant, antiallergic substances, and mixtures thereof.

12. The method of claim 1, wherein said fluid is a first fluid, and prior to applying said composition to said body, the method further comprises:
   applying a second fluid to said body, said second fluid being capable of penetrating into said cavities of said body; and
   wherein during the application of said composition, said composition significantly replaces said second fluid within said cavities.

13. The method of claim 1, wherein said fluid is a first fluid, and prior to applying said composition to said body, the method further comprises:
   applying a second fluid to said body, said second fluid being capable of penetrating into said cavities of said body;
   applying a third fluid to said body, said third fluid being capable of penetrating into said cavities of said body, wherein during the application of said third fluid, said third fluid significantly replaces said second fluid within said cavities; and
   wherein during the application of said composition, said composition significantly replaces said third fluid within said cavities.

14. The method of claim 12, wherein said second fluid has a contact angle with the surface of said body of not more than 90°.

15. The method of claim 12, wherein said second fluid has a viscosity of about 0.2 to about 10 centipoise at room temperature.

16. The method of claim 13, wherein said second fluid is miscible with said third fluid.

17. The method of claim 1, wherein said fluid is a first fluid, and prior to applying said composition to said body, the method further comprises:

applying a second fluid to said body, said second fluid being capable of penetrating into said cavities of said body;

applying a third fluid to said body, said third fluid being capable of penetrating into said cavities of said body, wherein during the application of said third fluid, said third fluid significantly replaces said second fluid within said cavities;

applying a fourth fluid to said body, said fourth fluid being miscible with said first and third fluids and being capable of penetrating into said cavities of said body, and wherein during the application of said fourth fluid, said fourth fluid significantly replaces said third fluid within said cavities; and wherein during the application of said composition, said composition significantly replaces said fourth fluid within said cavities.

18. The method of claim 17, wherein said third fluid is not miscible with said first fluid.

19. The method of claim 17, wherein said second fluid is not miscible with said fourth fluid.

20. The method of claim 1, wherein said pre-polymer is selected from the group consisting of polyethylene glycol diacrylate, unsaturated hyaluronic acid and pluronic.

21. The method of claim 1, further comprising removing essentially all of said fluid from said cavities, wherein said hydrogel remains in said cavities.

22. A method of impregnating an implantable device with a hydrogel, the method comprising:

(a) applying a composition to a substrate, said substrate having a body and interstices throughout said body, such that said composition penetrates into said interstices of said body of said substrate, said composition comprising a pre-polymer and a fluid;

(b) causing said pre-polymer to crosslink to form a hydrogel within said body of said substrate, wherein said causing comprises the act of curing said pre-polymer using a vehicle selected from the group consisting of light, heat and moisture curing at room temperature; and (c) removing essentially all of said fluid from said composition within said body of said substrate, wherein said hydrogel remains within said body of said substrate.

23. The method of claim 22, wherein when said curing is accomplished using light, and said composition further comprises a photoinitiator.

24. A method of impregnating an implantable device with a hydrogel, the method comprising:

(a) applying a composition to a substrate, said substrate having a body and interstices throughout said body, such that said composition penetrates into said interstices of said body of said substrate, said composition comprising a pre-polymer, a fluid and a therapeutic substance selected from the group consisting of antineoplastic, antiplatelet, anticoagulant, fibrinolytic, antimitotic, thrombin inhibitor, antiinflammatory, antiproliferative, antioxidant, and antiallergic substances, and mixtures thereof;

(b) causing said pre-polymer to crosslink to form a hydrogel within said body of said substrate; and (c) removing essentially all of said fluid from said composition within said body of said substrate, wherein said hydrogel and said therapeutic substance remain within said body of said substrate.

25. An implantable device having said hydrogel impregnated therein in accordance with the method of claim 24.

26. A method of impregnating an implantable device with a hydrogel, the method comprising:

(a) applying a first fluid to a substrate, said substrate having a body and interstices throughout said body, said first fluid being capable of penetrating into said interstices of said body;

(b) applying a second fluid to said substrate, said second fluid being capable of penetrating into said interstices of said body, wherein said second fluid significantly replaces said first fluid within said interstices;

(c) applying a composition to said substrate such that said composition penetrates into said interstices of said body of said substrate, said composition comprising a pre-polymer and a third fluid, wherein during the application of said composition, said composition significantly replaces said second fluid within said interstices;

(d) causing said pre-polymer to crosslink to form a hydrogel within said body of said substrate; and (e) removing essentially all of said third fluid from said composition within said body of said substrate.

27. An implantable device having said hydrogel impregnated therein in accordance with the method of claim 26.

28. The method of claim 26, wherein said pre-polymer is selected from the group consisting of PEG diacrylate, unsaturated hyaluronic acid, pluronic, and an absorbable PEG diacrylate hydrogel precursor.

29. The method of claim 28, wherein said first fluid is selected from the group consisting of acetone, isopropanol, ethanol and freon.

30. The method of claim 29, wherein said second fluid is water.

31. The method of claim 26, wherein said pre-polymer is selected from the group consisting of pluronic and an absorbable PEG diacrylate hydrogel precursor and wherein said hydrogel formed within said body of said substrate is a bioerodable hydrogel.

32. The method of claim 26, wherein said pre-polymer is PEG diacrylate and wherein PEG diacrylate is crosslinked with an unsaturated monomer.

33. The method of claim 32, wherein said unsaturated monomer is selected from the group consisting of vinyl pyrrolidone, acrylamide, phosphorylcholine, acrylic acid, dimethyl aminoethyl methacrylate (DMAMA), vinyl pyridine, methacrylic acid, and vinyl phosphonic acid.

34. The method of claim 33, wherein said composition additionally includes a therapeutic substance selected from the group consisting of antineoplastic, antiplatelet, anticoagulant, fibrinolytic, antimitotic, thrombin inhibitor, antiinflammatory, antiproliferative, antioxidant, and antiallergic substances, and mixtures thereof.

35. The method of claim 34, wherein said unsaturated monomer is positively-charged, and wherein said therapeutic substance is negatively-charged.

36. The method of claim 34, wherein said unsaturated monomer is negatively-charged, and wherein said therapeutic substance is negatively-charged.

37. The method of claim 22, wherein said substrate is selected from the group consisting of stents, grafts and coverings adapted to be disposed over a prosthesis.

38. The method of claim 22, wherein said pre-polymer is selected from the group consisting of PEG diacrylate, unsaturated hyaluronic acid, pluronic, and an absorbable PEG diacrylate hydrogel precursor.

39. The method of claim 22, wherein said pre-polymer is selected from the group consisting of pluronic and an absorbable PEG diacrylate hydrogel precursor and wherein said hydrogel formed within said body of said substrate is a bioerodable hydrogel.

40. The method of claim 22, wherein said pre-polymer is PEG diacrylate and wherein PEG diacrylate is crosslinked with an unsaturated monomer.

41. The method of claim 40, wherein said unsaturated monomer is selected from the group consisting of vinyl pyrrolidone, acrylamide, phosphorylcholine, acrylic acid, dimethyl aminoethyl methacrylate (DMAMA), vinyl pyridine, methacrylic acid, and vinyl phosphonic acid.

42. The method of claim 40, wherein said composition additionally includes a therapeutic substance.

43. The method of claim 42, wherein said unsaturated monomer is positively-charged, and wherein said therapeutic substance is negatively-charged.

44. The method of claim 42, wherein said unsaturated monomer is negatively-charged, and wherein said therapeutic substance is negatively-charged.

45. The method of claim 22, wherein said pre-polymer is crosslinked with an unsaturated monomer.

46. The method of claim 24, wherein said substrate is selected from the group consisting of stents, grafts and coverings adapted to be disposed over a prosthesis.

47. The method of claim 24, wherein said pre-polymer is selected from the group consisting of PEG diacrylate, unsaturated hyaluronic acid, pluronic, and an absorbable PEG diacrylate hydrogel precursor.

48. The method of claim 24, wherein said pre-polymer is selected from the group consisting of pluronic and an absorbable PEG diacrylate hydrogel precursor and wherein said hydrogel formed within said body of said substrate is a bioerodable hydrogel.

49. The method of claim 24, wherein said pre-polymer is crosslinked with an unsaturated monomer.

50. The method of claim 49, wherein said unsaturated monomer is selected from the group of vinyl pyrrolidone, acrylamide, phosphorylcholine, acrylic acid, dimethyl aminoethyl methacrylate (DMAMA), vinyl pyridine, methacrylic acid, and vinyl phosphonic acid.

51. The method of claim 49, wherein said unsaturated monomer is positively-charged, and wherein said therapeutic substance is negatively-charged.

52. The method of claim 49, wherein said unsaturated monomer is negatively-charged, and wherein said therapeutic substance is negatively-charged.

* * * * *